United States Patent [19]

Drewlow

[11] Patent Number: Plant 6,427

[45] Date of Patent: Nov. 29, 1988

[54] BEGONIA PLANT NAMED ENCHANTMENT

[75] Inventor: Lyndon W. Drewlow, Ashtabula, Ohio

[73] Assignee: Mikkelsens, Inc., Ashtabula, Ohio

[21] Appl. No.: 20,762

[22] Filed: Mar. 2, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A Begonia plant named Enchantment, characterized by its salmon orange flower color, semi-double flower form, cyme type inflorescence; compact, upright growth habit with good branching, early flowering, ease of propagation by stem and leaf cuttings, and excellent flower retention during shipping.

1 Drawing Sheet

The present invention relates to a new and distinctive cultivar of Begonia plant, botanically known as *Begonia hiemalis,* Fotsch, and known by the cultivar name Enchantment.

The new cultivar was discovered by me as a seedling from a controlled crossing of *B. tuberhybrida,* Mikkelsen Seedling No. 84-617-4, as the seed parent with *B. socotrana,* Mikkelsen Seedling No. 84-1018-26, as the pollen parent.

Asexual reproduction of Enchantment by stem and/or leaf cuttings by me at Ashtabula, Ohio, has reproduced the unique features of the new cultivar through successive propagations.

The following characteristics distinguish the new begonia from both its parents and other begonias commercially known and used in the floriculture industry. In describing Enchantment, comparisons have been made with other cultivars, including Tango (U.S. Plant Pat. No. 5,538), Whisper-of-Pink (U.S. Plant Pat. No. 3,787), and Revelry, Bolero and Alice, all of which are not patented.

1. Enchantment is salmon orange in color, being close to the color of Tango and Revelry. Bolero has more orange, Alice is more salmon pink, and Whisper-of-Pink has more pink.

2. Enchantment is a semi-double cultivar while Alice and Whisper-of-Pink are single. Tango, Revelry and Bolero are full doubles.

3. Flower size of Enchantment is larger than Alice and Bolero, equal to Whisper-of-Pink and Revelry, and slightly smaller than Tango.

4. Plant height of Enchantment is more compact than Whisper-of-Pink, similar to Bolero and Revelry, and Alice and Tango are more compact.

5. Leaf size is similar to Revelry and Whisper-of-Pink. Tango, Bolero and Alice have smaller leaves.

6. Whisper-of-Pink and Alice have brighter green leaves, Bolero has darker green leaves, and Tango and Revelry have a similar intermediate green leaf color as Enchantment.

7. Lobes of the leaf overlap both on mature and immature leaves, like Alice and Whisper-of-Pink. Only mature leaves overlap in Revelry and Bolero, and neither mature or immature leaves overlap in Tango.

8. The immature leaf of Enchantment has a red margin with the remainder of the leaf being green, similar to Alice and Whisper-of-Pink. Tango, Bolero and Revelry all have a more distinct red margin and some red coloring infused in the back of the leaf.

9. Enchantment has a cyme type of inflorescence which is similar to Whisper-of-Pink, while Bolero, Alice, Revelry and Tango have a raceme type of inflorescence.

10. Early flowering.

11. Heavy branching from base of plant after stem cutting has been pinched.

12. Excellent holding of flowers on plant when being shipped.

13. Propagates well from stem and leaf cuttings.

14. Good balance between leaf size and plant size.

15. Suitable for 12, 15 and 25 cm pot plant production.

The accompanying colored photograph illustrates in perspective view the overall appearance of Enchantment, showing the colors as true as it is reasonably possible to obtain in a colored reproduction of this type.

The following is a detailed description of my new begonia cultivar based on plants produced under commercial practices in Ashtabula, Ohio, under greenhouse conditions. The photograph was taken in early June, 1986, and color references are made to The Royal Horticultural Society Colour Chart except where general color terms of ordinary dictionary significance are used.

Parentage: A controlled cross between *B. tuberhybrida,* Mikkelsen Seedling No. 84-617-4×*B. Socotrana,* Mikkelsen Seedling No. 84-1018-26.

Propagation:

(A) *Type cutting.*—Leaf.

(B) *Time to root.*—18 days at 21° C. summer; 24 days at 21° C. winter.

(C) *Rooting habit.*—Numerous, fibrous, fine.

(D) *Time for shoot development.*—10 weeks in summer to 13 weeks in winter to obtain shoots 4 to 5 cm long in length.

Plant description:

(A) *Form.*—Upright, good stem strength for self-support, compact, short internodes, well branched. Suitable for 10, 15 and 25 cm pot plant production.

(B) *Habit of growth.*—Vigorous, fast upright growth, early to flower, good branching from base of plant when pinched. Usually vegetative shoots are formed at the basal nodes and flower shoots at the higher nodes.

(C) *Foliage.*—Leaves simple, alternate, borne on strong petioles 5–6 mm in diameter on mature basal leaves. (1) Size: Mature basal leaves are 10 to 11 cm in diameter. Size can vary with position on plant, number of shoots per plant, and environment. (2) Shape: Ovate to almost orbicular, lobes overlap on both mature leaves and immature leaves. (3) Texture: Leathery, glabrous. (4) Margin: Serrated. (5) Color: Young foliage, top side 146B, with red tint to margin; Young foliage, under side 146C, red tint at margins. Mature foliage, top side 147A and 147B; Mature foliage, under side 148B. (6) Venation: Palmate with 6 major veins.

Flowering description:

(A) *Flowering habits.*—Flowering in cymes, five being the most common number of flowers per cyme. Several flowers are in bloom at one time on plant, with flowering continuing more or less indefinitely.

(B) *Natural flowering season.*—Will flower year around without controlling day length. Plants will flower earlier and more abundantly if subjected to a reduced day length of 12 hours.

(C) *Flower buds.*—20 mm wide and 15 mm long just before opening. Tepals are slightly crenated at margins. Color 47C just before opening; 46C when immature.

(D) *Flowers borne.*—On strong upright peduncles 5 mm in diameter, with a reddish cast to the green. Pedicels on which flowers are borne are a shade deeper red in color and vary in length in the cyme.

(E) *Quantity.*—Five (5) per peduncle is the average, opening in sequence as the cyme develops. Total number per plant will vary with number of flowering shoots that develop.

(F) *Tepals.*—(1) Shape: Flat and heart shaped, crenate at tips. (2) Color top side in summer when opening: 39A, fading to 35B-C; underside 43C. (3) Number of tepals: 20 or more; semi-double. (4) Size of tepals: 25 mm long and 20–22 mm wide at widest part. (5) Flower size: 50–55 cm in diameter (first one to open in cyme).

(G) *Reproductive organs.*—(1) Stamens: Many. (a) Anther shape: Rounded, color yellow. (b) Pollen color: No pollen present. (2) Pistils: No female flowers observed to date.

Disease resistance: Enchantment has shown good resistance to powdery mildew. No other disease and insect problems have been observed to date.

I claim:

1. A new and distinct Begonia plant named Enchantment, as illustrated and described, and particularly characterized by its salmon orange flower color, semi-double flower form, cyme type inflorescence; compact, upright growth habit with good branching, early flowering, ease of propagation by stem and leaf cuttings, and excellent flower retention during shipping.

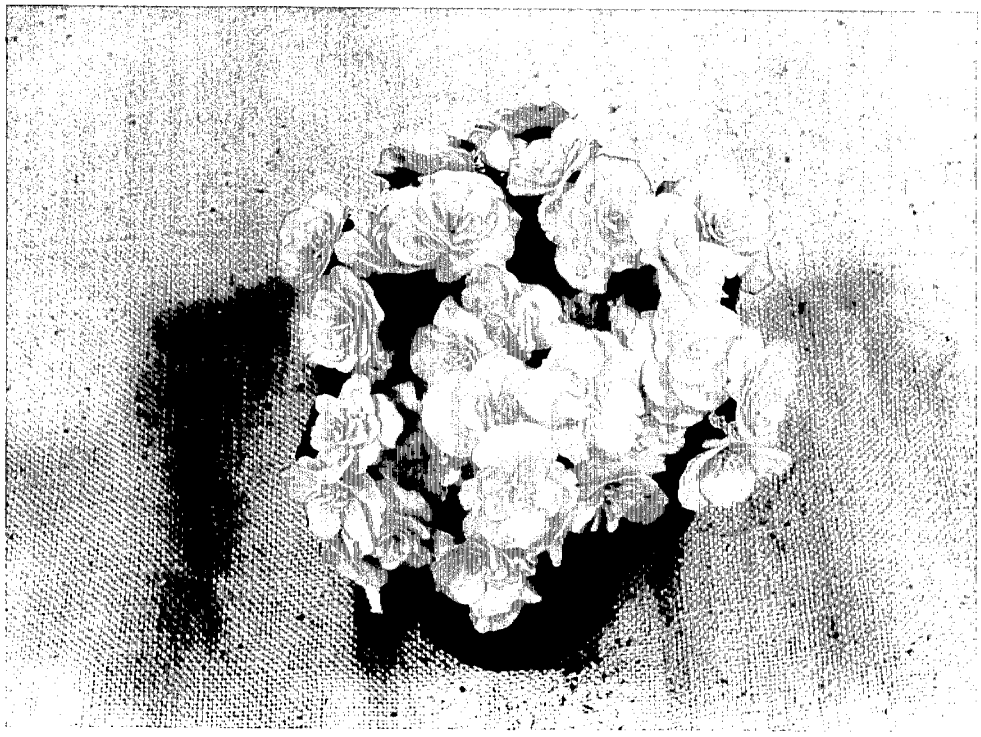

* * * * *